United States Patent [19]
Moll et al.

[11] Patent Number: 5,671,729
[45] Date of Patent: Sep. 30, 1997

[54] ANESTHETIC EVAPORATOR

[75] Inventors: Stefan Moll; Uwe Bausch; Stefan Linke; Dirk-Stefan Reichert; Karl-Ludwig Gippert, all of Lübeck; Wolfgang Falb, Krummesse, all of Germany

[73] Assignee: Drägerwerk Aktiengesellschaft, Lübeck, Germany

[21] Appl. No.: 730,967

[22] Filed: Oct. 16, 1996

[30] Foreign Application Priority Data

Apr. 6, 1996 [DE] Germany ............... 196 13 754.3

[51] Int. Cl.$^6$ .................................................. A61M 16/00
[52] U.S. Cl. .............................. 128/203.14; 128/204.13
[58] Field of Search ....................... 128/203.12, 203.14, 128/203.25, 203.26, 203.27, 204.21, 204.22

[56] References Cited

U.S. PATENT DOCUMENTS 4,345,612  8/1982  Koni et al. ................. 128/203.25
5,490,500  2/1996  Reichert et al. ............. 128/204.13

FOREIGN PATENT DOCUMENTS 10 98 169   1/1961   Germany.

*Primary Examiner*—Vincent Millin
*Assistant Examiner*—Robert N. Wieland
*Attorney, Agent, or Firm*—McGlew and Tuttle

[57] ABSTRACT

A device for mixing anesthetic vapor with a gas according to the bypass principle such that anesthetic gas or liquid anesthetic is prevented from escaping from the evaporator chamber during transportation. The switching on of the anesthetic evaporator takes place under defined pressure conditions in the evaporator chamber. A transport position, which precedes the switch-off position, and in which a ventilating valve of a ventilating line arriving from the evaporator chamber is switched into the switch-off position by the setting member, is provided on the setting member.

1 Claim, 1 Drawing Sheet

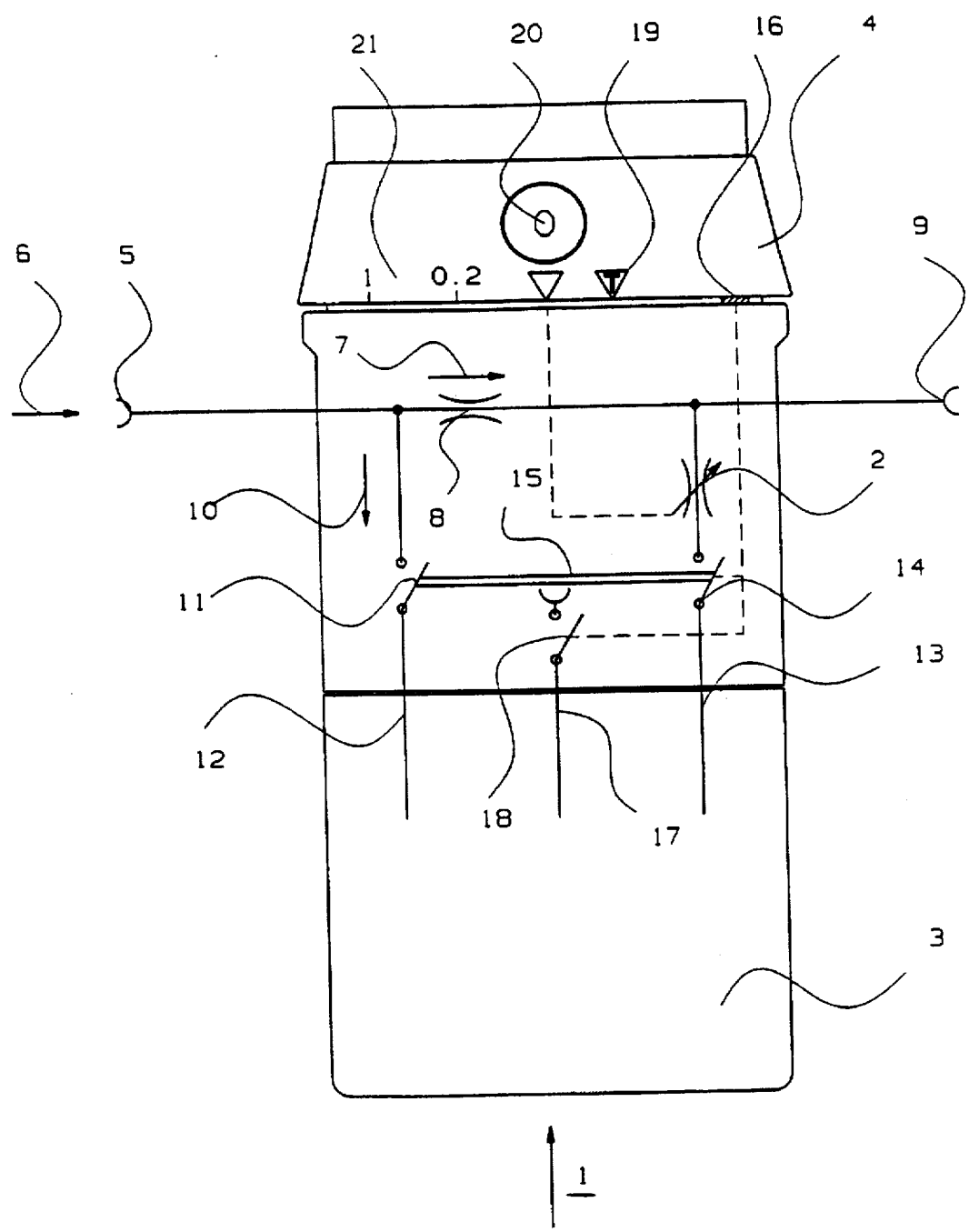

ANESTHETIC EVAPORATOR

The present invention pertains to a device for mixing anesthetic vapor with a gas according to the bypass principle, in which the gas to be enriched with the anesthetic vapor reaches an outlet opening via both a bypass channel and an evaporator chamber generating the anesthetic vapor, with valves at an inlet and at an outlet of the evaporator chamber, with a metering unit for mixing anesthetic vapor with the gas, with a setting member actuating the metering unit, by which the valves are switched into the switch-off position in a switch-off position of the setting member, and with a ventilating line leading from the evaporator chamber into the environment via a ventilating valve.

BACKGROUND OF THE INVENTION

An anesthetic evaporator with a metering unit, an evaporator chamber, and a setting member actuating the metering unit has become known from German Auslegeschrift No. DE-AS 10 98 169. The gas to be enriched with the anesthetic flows through the evaporator chamber in the prior-art anesthetic evaporator from a gas inlet to a gas outlet. A slide valve, by which the evaporator chamber is completely separated from the metering unit and from the gas flow flowing through the evaporator in the shutoff position of the setting member, is provided at the inlet and at the outlet of the evaporator chamber. In this position of the slide valve, the evaporator chamber is in connection with the ambient air only via a ventilating channel.

The disadvantage of the prior-art anesthetic evaporator is that anesthetic liquid may escape from the evaporator chamber during transportation if the apparatus is tilted, that anesthetic enters the area of the vent hole, and that an overpressure builds up during transportation in the evaporator chamber because of the vent hole being closed by the anesthetic liquid. Since anesthetics are substances with relatively low boiling points, such a state may develop in the evaporator chamber even as a result of an increase in the ambient temperature. However, the evaporator chamber shall be possibly pressureless when the anesthetic evaporator is put into operation when it is connected to the gas flow via the slide valve. An evaporator chamber under overpressure would release an uncontrolled amount of anesthetic vapor into the gas flow when connected to the metering device.

SUMMARY AND OBJECTS OF THE INVENTION

The primary object of the present invention is to improve an anesthetic evaporator of the above-described type such that gaseous or liquid anesthetic is prevented from escaping from the evaporator chamber during transportation, and the anesthetic evaporator is switched on under defined pressure conditions in the evaporator chamber.

This object is accomplished by a switch-off position, in which the ventilating valve is switched by the setting member into the closed position, being provided on the setting member.

The advantage of the present invention is essentially the fact that in addition to the switch-off position, the so-called zero position of the setting member, a transport position is provided on the setting member, in which position the ventilating valve of the evaporator chamber is switched into the switch-off position. It is achieved as a result that the evaporator chamber is completely separated from the environment in the transport position. The transport position is preferably arranged on the setting member as a position preceding the switch-off position. For putting into operation, the adjusting member is first switched from the transport position into the switch-off position, and the ventilating valve is thus brought into the flow direction. The overpressure present in the evaporator chamber can escape into the environment or into a line through which anesthetic gas is removed. In the case of vacuum in the evaporator chamber, the pressure is equalized in the opposite direction. If the setting member is now set at a defined concentration value, the ventilating valve is first closed, and the flow of gas through the evaporator chamber is established by opening the valves located at the inlet and at the outlet.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS In the drawings:

The only FIGURE is a schematic view of an anesthetic evaporator according to the invention.

DESCRIPTION OF THE PREFERRED EMBODIMENT

Referring to the drawing in particular, the only FIGURE schematically shows an anesthetic evaporator 1 with a metering unit 2, with an evaporator chamber 3, and with a setting member 4, which sets the metering unit 2 to the desired concentration value. The gas flow 6 entering at a gas inlet opening 5 is divided into a bypass gas flow 7, which will again directly reach a gas outlet opening 9 via a bypass valve 8, and an evaporator chamber gas flow 10. The evaporator chamber gas flow 10 flows into a first inlet 12 of the evaporator chamber 3 via a first valve 11. The gas enriched with anesthetic vapor reaches the metering unit 2 from an outlet 13 of the evaporator chamber 3 via a second valve 14. The valves 11, 12 are actuated simultaneously via a connecting element 15, so that either there is a flow connection leading the evaporator chamber gas flow 10 from the inlet 12 to the metering unit 2 via the outlet 13, or, as is shown in the FIGURE, the evaporator chamber 3 is completely separated from the gas flow. The valves 11, 14 are actuated via a trip cam 16 on the setting member 4. A ventilating line 17, which opens into the environment via a ventilating valve 18, is connected to the evaporator chamber 3. The ventilating valve 18 is also actuated via the trip cam 16 on the setting member 4.

Various setting positions of the anesthetic evaporator 1 are indicated on the setting member 4. These setting positions are a transport position 19, a zero position 20, and a concentration-setting range 21. In the transport position 19, which is illustrated in the FIGURE, the valves 11, 14, 18 are in the switch-off position, in which the evaporator chamber 3 is completely isolated from the environment and from the gas inlet opening 5 and from the gas outlet opening 9. With the transition from the transport position 19 into the zero position 20, the ventilating valve 18 is switched into the flow direction by the trip cam 16, while the valves 11, 14 remain in the switch-off position. An overpressure that may be present in the evaporator chamber 3 due to evaporated anesthetic can be released into the environment by opening the ventilating valve 18. If the setting member 4 is switched over from the zero position 20 into the concentration-setting range 21, the ventilating valve 18 is closed by the trip cam 16, and the valves 11, 14 are switched into the flow direction. Only the evaporator chamber gas flow 10 can now reach the metering unit 2 via the evaporator chamber 3. More or less anesthetic vapor is mixed with the bypass gas flow 7 by changing the opening cross section of the metering unit 2 via the setting member 4.

The advantage of the anesthetic evaporator 1 according to the present invention is essentially that the evaporator chamber 3 is completely separated from the metering unit 2 and the environment in the transport position 19, so that neither liquid anesthetic nor anesthetic vapor can escape from the evaporator chamber 3 during transportation. The evaporator chamber 3 is first ventilated to the environment via the ventilating valve 18 when the anesthetic evaporator 1 is put into operation, i.e., at the time of the transition from the transport position 19 into the zero position 20. The ventilating valve 18 is closed again at the time of the change from the zero position 20 into the concentration-setting range 21, and the valves 11, 14 are switched into the flow direction. Due to the pressure relief of the evaporator chamber 3 in the zero position 20, flow through the evaporator chamber 3 is possible at the pressure level of the gas flow 6 at the time of the transition of the setting member 4 into the concentration-setting range 21.

While a specific embodiment of the invention has been shown and described in detail to illustrate the application of the principles of the invention, it will be understood that the invention may be embodied otherwise without departing from such principles.

What is claimed is:

1. A device for mixing anesthetic vapor with a gas according to the bypass principle, comprising:

an evaporator chamber generating the anesthetic vapor, said evaporator chamber having an evaporator chamber inlet and an evaporator chamber outlet;

a device outlet opening a bypass channel, gas to be enriched with the anesthetic vapor reaching said outlet opening via both said bypass channel and said evaporator chamber;

a valve at a said evaporator chamber inlet and a valve at said evaporator chamber outlet;

a ventilating valve;

a ventilating line leading from the said evaporator chamber into the environment via said ventilating valve;

a metering unit for mixing the anesthetic vapor with the gas; and a setting member actuating said metering unit and switchable to a switch-off position and a transport position, said valve at said evaporator chamber inlet and said valve at said evaporator chamber outlet being switched into a switch-off position in said switch-off position of said setting member and said ventilating valve being switched by the said setting member into a switch-off position in said transport position of said setting member.

* * * * *